US011903862B2

(12) United States Patent
Tüttemann et al.

(10) Patent No.: US 11,903,862 B2
(45) Date of Patent: Feb. 20, 2024

(54) DEVICE FOR SUPPORTING A BACK OF A USER (71) Applicant: Ottobock SE & Co. KGaA, Duderstadt (DE)

(72) Inventors: Markus Tüttemann, Waltrop (DE); Carsten Vogel, Duderstadt (DE); Paul Weber, Wiesbaden (DE); Oliver Mizera, Göttingen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 92 days.

(21) Appl. No.: 17/094,983

(22) Filed: Nov. 11, 2020

(65) Prior Publication Data

US 2021/0137720 A1 May 13, 2021

(30) Foreign Application Priority Data

Nov. 11, 2019 (DE) ...................... 10 2019 130 389.3

(51) Int. Cl.
*A61F 5/02* (2006.01)
*A61F 5/37* (2006.01)
(52) U.S. Cl.
CPC ............ *A61F 5/028* (2013.01); *A61F 5/3715* (2013.01)
(58) Field of Classification Search
CPC .. A61F 5/00; A61F 5/01; A61F 5/0102; A61F 5/0123; A61F 5/0125; A61F 5/02;
(Continued)

(56) References Cited

U.S. PATENT DOCUMENTS 654,173 A 7/1900 Mendenhall
1,409,326 A 3/1922 Williamson
(Continued)

FOREIGN PATENT DOCUMENTS

DE 102 38 256 A1 3/2004
DE 10 2012 013 141 A1 5/2014
(Continued)

OTHER PUBLICATIONS

Cruzan, Jeff, Hooke's Law, 2017, [online], [Retrieved on Mar. 15, 2023], Retrieved from the Internet URL<https://xaktly.com/HookesLaw.html (Year: 2017).*

(Continued)

*Primary Examiner* — Ophelia A Hawthorne
*Assistant Examiner* — Gina McCarthy
(74) *Attorney, Agent, or Firm* — WCF IP (57) ABSTRACT The invention relates to an orthopedic device for supporting a back, especially a lower back, of a user, wherein the device comprises
an upper body element 48,
an upper leg element 4 and
a first passive actuator 8, which is configured to apply a force to the upper leg element 4 and/or the upper body element 48 when an angle between the upper leg element 4 and the upper body element 48 is within a first predetermined angular range, wherein the device comprises at least a second passive actuator 10, which is configured to apply a force to the upper leg element 4 and/or the upper body element 48 when the angle is within a predetermined second angular range that is different to the first angular range.

25 Claims, 8 Drawing Sheets (58) Field of Classification Search
CPC .......... A61F 5/022; A61F 5/024; A61F 5/026; A61F 5/028; A61F 5/03; A61F 5/04; A61F 5/042; A61F 5/3715; A61F 2005/0179; A61F 2005/0132; A61F 2/64; A61F 2/68; A61F 4/00; A61H 1/02; A61H 1/0218; A61H 1/0292; A61H 2201/1619; A61H 2201/1621; A61H 2201/1623; A61H 2201/1626; A61H 2201/1628; A61H 1/0229; A61H 3/00; A63B 21/4025; B25J 9/108; A61B 5/1126
See application file for complete search history.

(56) References Cited

U.S. PATENT DOCUMENTS

| | | | |
|---|---|---|---|
| 4,856,500 A * | 8/1989 | Spademan | A61F 5/0125 602/26 |
| 7,344,569 B2 | 3/2008 | Imakita et al. | |
| 2007/0027419 A1* | 2/2007 | Drennan | A63B 21/4025 602/19 |
| 2014/0378882 A1* | 12/2014 | Kazerooni | A61H 3/00 602/19 |
| 2015/0164660 A1 | 6/2015 | Will et al. | |
| 2016/0113831 A1* | 4/2016 | Hollander | A61H 3/00 623/32 |
| 2016/0250062 A1* | 9/2016 | Radaelli | A61F 5/028 602/16 |
| 2017/0360588 A1* | 12/2017 | Yangyuenthanasan | A61F 5/028 |
| 2019/0091093 A1* | 3/2019 | Lee | A61F 5/0102 |
| 2020/0093676 A1* | 3/2020 | Mizera | B25J 9/108 |
| 2021/0315514 A1* | 10/2021 | Schmidt | A61B 5/1126 |

FOREIGN PATENT DOCUMENTS

| | | |
|---|---|---|
| WO | 2016/148566 A1 | 9/2016 |
| WO | 2018/136722 A1 | 7/2018 |

OTHER PUBLICATIONS

Ryan, Johnson, Elastic Modulus: Elasticity, Uses, How to Measure, Feb. 3, 2022 [online], [retrieved on Mar. 14, 2023], Retrieved from the Internet <URL: https://study.com/learn/lesson/elastic-modulus-overview-uses.html (Year: 2022).*

Tension Springs Explained, 2023 [online], [retrieved on Mar. 14, 2023], Retrieved from the Internet <URL: https://www.springsfast.com/resources/blog/tension-springs-explained/#:~: text=Tension%20springs%20are%20wound%20helical,apart%20from%20its%20original%20length. (Year: 2023).*

Spring Constant Formula Using Hooke's Law, Mar. 12, 2023 [online], [retrieved on Mar. 14, 2023], Retrieved from the Internet <URL: https://www.vedantu.com/formula/spring-constant-formula (Year: 2023).*

What is elastic potential energy?, 2023 [online], [retrieved on Mar. 14, 2023], Retrieved from the Internet <URL: https://www.khanacademy.org/science/physics/work-and-energy/hookes-law/a/what-is-elastic-potential-energy (Year: 2023).*

International Search Report; PCT/EP2020/080910; dated Jan. 4, 2020.

* cited by examiner

DEVICE FOR SUPPORTING A BACK OF A USER

The invention relates to an orthopedic device for supporting a back, especially a lower back, of a user, wherein the device preferably features an upper body element, an upper leg element and a first passive actuator, which is configured to apply a force to the upper leg element and/or the upper body element when an angle between the upper leg element and the upper body element is within a first predetermined angular range.

Devices for supporting a lower back have been known from the prior art for many years and should be used in particular to relieve the lower back if, for instance, heavy objects are to be lifted and carried. U.S. Pat. No. 443,113 describes a device that features leaf spring elements, of which one end is fixed in the shoulder region and the other is fixed on the upper leg of a person. If the wearer of such a device bends over, the leaf spring is bent and thus tensioned. It then exerts a force that supports the wearer of the device when he straightens up.

Another device is described in US 2017/0360588 A1. It features a leg support element with a leg shell for mounting on the front side of the upper leg. The counter bearing is designed in the form of a breastplate, which pushes against the chest of the wearer of the device. When the two elements are swivelled against each other, a spring device is tensioned, thereby generating a return force that should help the wearer of the device to straighten up.

WO 2014/195373 A1 describes another device with which the wearer of the device should be supported when lifting heavy objects. With this device, the entire body of the wearer is supported, including the arms and legs.

The disadvantage is that the known devices either apply the same force across an entire angular range in which the actuators apply a force, or that the force is only applied over a single angular range and in this range first increases and then decreases again as the angle increases. Experience shows that the device is required for two different movement sequences, but can only be adjusted to one of them. The first movement sequence involves lifting objects, such as luggage or parcels, from a surface at half height, such as a table. As a result, the person using the orthopedic device only works in a small angular range without, for example, bending over completely or lifting anything up off the floor. This also relates to people who have to work for long periods in a slightly bent position, for example over a table. Such work is carried out by surgeons or fitters, for example. The second type of movement involves lifting heavy objects, such as luggage or parcels, from the floor or a similar low surface. The orthopedic device is also required in this case, but the angular range in which the force is to be applied is completely different from that of the first movement sequences.

The invention thus aims to further develop an orthopedic device according to the generic term in claim 1 in such a way that it can be used flexibly and as comprehensively as possible and can preferably be individually adjusted.

The invention solves the problem by way of an orthopedic device according to the generic term in claim 1, characterized in that the device comprises at least a second passive actuator that is configured to exert a force on the upper leg element and/or the upper body element when the angle is within a predetermined second angular range, which is different to the first angular range.

The skilled selection of the first angular range and the second angular range allows the device according to the invention to be used, for instance, for both movement sequences described above. If the wearer of the orthopedic device bends only a little, for example, or works in a bent position, this preferably corresponds to the first angular range, so that the first passive actuator exerts the necessary force. However, if the wearer of the orthopedic device bends to pick something up off the ground, for instance, the resulting angle between the upper leg element and the upper body element preferably corresponds to the second angular range, so that the second passive actuator exerts the force.

The first and second angular range preferably overlap. In other words, there are angles between the upper leg element and the upper body element at which both passive actuators exert a force.

Preferably, the first passive actuator and/or the second passive actuator comprise(s) at least one mechanical energy store and/or one damper. For example, this can be an elastic element such as a spring element, preferably a tension spring. The first passive actuator and/or the second passive actuator may be designed to transmit a constant force across the respective angular range in which the respective actuator exerts the force. To this end, the respective actuator may have, for instance, a constant force spring. Alternatively or additionally, however, the actuator can also be designed in such a way that a force that increases as the angle decreases, rather than a constant force, is applied within the respective angular range. A decreasing angle means a more pronounced bend, so that in this case, the force exerted by the respective actuator increases the deeper the user of the device bends down. In another configuration, the force can also exhibit its maximum at an angle within the respective angular range and drop at larger angles and at smaller angles.

The first and second passive actuator are preferably designed to be different. Specifically, the elastic elements of both actuators may exhibit different elasticities, in particular different spring constants, and/or different degrees of damping. In addition, they may also be different lengths, wherein the length of the elastic element is measured in the slackened state.

Preferably, the first passive actuator and/or the second passive actuator are arranged at at least one point of application on the upper leg element and/or the upper body element, each of which is adjustable. In this way, the respective predetermined angular range, within which the respective actuator exerts the force, can be adjusted. In addition, a preload of the respective passive actuator can be achieved, so that the size of the respective force to be applied can be adjusted.

To be able to apply different forces, it is advantageous if the first passive actuator and the second passive actuator are arranged at different points of application on the upper leg element and/or the upper body element and/or they have different lengths.

As such, when the device is mounted, it is particularly easy to recognize which actuator exerts its force in which angular range and/or which actuator exerts a greater or smaller force. Of course, it is also possible to have both actuators strike at the same point of application or to use two actuators of the same length. This is possible, for example, if both actuators have different spring constants and/or elasticities.

In a preferred configuration, the upper body element features a first force transmission element and the upper leg element a second force transmission element. Both force transmission elements can be engaged with and disengaged from one another. The first mechanical energy store and the second mechanical energy store can be charged and discharged by swivelling the upper leg element relative to the upper body element, provided that the first force transmission element is engaged with the second force transmission element. Otherwise, the upper leg element and the upper body element can be swivelled against each other without charging one of the two mechanical energy stores with energy. This configuration renders it possible to swivel the upper leg element relative to the upper body element without charging the respective energy store with energy. In this state, no force is exerted by the energy store, i.e. the respective passive actuator. This is advantageous for certain movement sequences. If the user of the device climbs a step, for instance, he must raise his upper legs and therefore also the upper leg elements arranged on the upper legs. In other words, he has to swivel an upper leg element relative to the upper body element. If the two force transmission elements were engaged with one another in this state, raising the upper leg element would charge the mechanical energy store and extending the leg to the next step would discharge it again. However, if the device is not to provide support when climbing stairs, it is advisable to allow the two force transmission elements to disengage during this movement.

In many cases, the support offered by the orthopedic device should only be provided when lifting or standing up from a squatting position. To guarantee this, it must be ensured that the two force transmission elements only engage with each other in these states. This can be achieved, for example, by having a pelvic element and bringing the two force transmission elements into engagement with one another as soon as an angle between the pelvic element or a component of the pelvic element and the upper body element exceeds a predetermined limit angle.

The device therefore preferably has a pelvic element, wherein the upper body element is movably arranged relative to the pelvic element. In this case, the first force transmission element is engaged with and disengaged from the second force transmission element by moving the upper body element relative to the pelvic element. If the angle between the pelvic element and the upper body element gets reduced below a predetermined limit angle, the two force transmission elements are brought into engagement with each other. If the angle then exceeds the predetermined limit angle, the force transmission elements are disengaged again.

In preferred configurations, the first passive actuator and the second passive actuator are each arranged at one force application point on one force application lever. This is preferably arranged on the pelvic element or the upper body element. In these configurations, the two passive actuators preferably act on the upper leg element, i.e. they are arranged with one of their ends on the upper leg element and with the other end on the respective force application lever. If the two force transmission elements are disengaged, the force application levers can be freely swivelled relative to the pelvic element. If the upper leg element is swivelled relative to the pelvic element and thus also relative to the upper body element in this state, the force transmission levers follow this swivelling, such that the passive actuators and the mechanical energy stores preferably contained within them are not charged with energy. This results in no force and no support.

However, if the two force transmission elements do engage with each other, the force transmission levers are positioned on the pelvic element such that they are torque-proof and can no longer follow the swivel movement of the upper leg element. The distance between the force application point on the force application lever on the one hand and the point of application on the upper leg element on the other thus increases with the movement, so that the mechanical energy store is charged with mechanical energy and exerts a supporting force.

Preferably, an orientation and/or position of the two force transmission levers in relation to one another and/or at least one of the two, but preferably both, force application points is adjustable. The movement, for instance swivelling, of the two force application levers relative to each other enables the adjustment of the angular range in which the respective passive actuator exerts its force. A displacement of the force application point on the force application lever, for instance towards the swivel axis of the upper leg element relative to the pelvic element or away from it, enables the adjustment of the strength of the force to be applied. By adjusting the force application point on the force application lever differently, for instance in the circumferential direction with respect to the above-mentioned swivel axis, it is also possible to achieve a preload of the respective passive actuator.

A preload of the first actuator and/or a preload of the second actuator is preferably adjustable.

Preferably, the pattern of force applied by the first actuator and/or the force applied by the second actuator extends depends on the angle; in particular, said pattern is curved, especially preferably sinusoidal.

Preferably the force exerted by the first actuator and the force exerted by the second actuator exhibit a maximum at different angles.

For angles smaller than the respective predetermined angular, the force exerted by the respective actuator is preferably zero, or essentially zero. In this case, the more the upper body is bent relative to the upper leg, the smaller the angle.

Preferably, the first and second passive actuator each act on one force application lever. The two force application levers are preferably designed to be length-adjustable, so that the size of the torque applied by the respective actuator or the strength of the respective force can be adjusted. Additionally or alternatively, the force application levers are designed to be adjustable relative to each other and/or relative to a pelvic element so that the position of the predetermined first angular range and/or the position of the predetermined second angular range can be adjusted. When the upper body element bends relative to the upper leg element, the respective actuator, which can be a spring element for instance, is charged with mechanical energy and can thus exert the force. Here, the distance between the first end of the respective actuator and the second end of the actuator is greater.

The device preferably features an end stop, which can be arranged on a pelvic element, for example, and on which the first passive actuator and/or the second passive actuator strikes when the respective force application lever has reached a certain position, especially relative to the upper leg element. As a result, the respective actuator is still tensioned and charged with mechanical energy, but said energy preferably acts directly on the rotational axis between the upper body element and the upper leg element, provided that the end stop is arranged on this rotational axis. A force is thus exerted but it no longer leads to a torque; therefore, it also does not lead to a support of the back.

The orthopedic device for supporting a lower back of a user comprises at least one mechanical energy store, a pelvic element, a torso element and an upper leg element, wherein the mechanical energy store can be charged and discharged by swivelling the upper leg element relative to the torso element. Preferably, the upper body element is arranged on the pelvic element by means of two rail elements, wherein the rail elements are each arranged with a first end on the pelvic element such that they can swivelled about at least a first swivel axis and with a second end opposite the first end on the upper body element such that they can be swivelled about at least a second swivel axis.

The pelvic element is preferably designed as a pelvic harness or hip harness and therefore extends fully around the body at the height of the pelvis or hips. Between the two first ends of the two rail elements, which are arranged on the pelvic element, extends a part of the pelvic element, which is preferably not or at least largely not variable in length when the device is in use. In a structurally simple and therefore preferred configuration, the distance between the first end and the second end of the respective rail element is also designed to be not or at least largely not variable in length when the device is in use. This also applies for the distance between the two second ends of the rail elements. This results in a parallelogram which, due to the articulated arrangement of the respective parts, is movable. In a preferred embodiment, the freedom of movement of the user's upper body and in particular the user's spinal column is not or at least largely not restricted.

Preferably, at least one of the specified variables is designed to be adjustable. The respective variable can therefore be adjusted to fit a body part of the user. After adjustment, it is set to the individually desired value and then fixed, e.g. locked, in such a way that it does not change or at least largely does not change when the device is used. It is preferable if several, but especially preferable if all, specified variables can be adjusted and locked in this manner.

It is particularly preferable if the upper body element is arranged on the pelvic element in such a way that the lateral flexion of the spinal column and the rotation of the spinal column about a rotational axis in the sagittal plane is possible. In this case, the freedom of movement of the spinal column of the user is not restricted at all, so that all movements that the user of the orthopedic device can execute with his spinal column without the orthopedic device are also possible with the orthopedic device.

A rotational axis in the sagittal plane is understood particularly to mean a vertical rotational axis which lies in the median plane, and thus in the central sagittal plane, when a user is standing up straight. It could also be described as the longitudinal axis of the spinal column, wherein the spinal column of a human, due to its geometric form, does not have a longitudinal axis in the mathematical sense. Of course, rotational axes displaced parallel to this axis also lie in a sagittal plane.

If the freedom of movement of the user's spine is not restricted by the device, it is understood particularly to mean that both flexion and extension are possible. These movements are also referred to as ventral flexion and dorsal extension, or inclination and reclination. A flexion is the leaning forward of the upper body, and thus of the spinal column and the head, while extension is the opposite movement. In this case, other movements of the upper body and therefore the spinal column, such as lateral flexion and rotation, are also not restricted by the orthopedic device.

Movements of the spinal column, particularly a leaning of the spinal column to the side and/or forwards and backwards and/or a twisting of the spinal column about its longitudinal axis, are preferably also not prevented, restricted or rendered impossible by the orthopedic device. All of the movements described here are preferably restricted by the orthopedic device in neither their maximum movement deflection nor in a sequence of movement.

If the upper leg element is swivelled relative to the upper body element in a first direction, the mechanical energy store, which can be, for instance, an elastic element such as a tension spring, is charged with energy. The first direction corresponds, for example, to raising the upper leg element, for instance to climb a step. However, it is preferable to have the device in a deactivated state when climbing stairs, so that no supporting force is applied when climbing stairs. Bending forward (flexion) of the upper body also swivels the upper body element relative to the upper leg element accordingly. The first direction is thus characterized in that an angle between the upper leg element and the upper body element decreases due to the swivelling.

The energy that charges the mechanical energy store can be, for instance, an elastic or potential energy. In this state, the mechanical energy store preferably applies a force to the upper leg element and/or the upper body element which acts in the second direction that is opposite to the first. If the upper leg element is swivelled relative to the upper body element in this second direction, the mechanical energy store is discharged and the energy released supports the movement of the upper leg element relative to the upper body element. This second direction refers, for instance, to the lowering of the upper leg element or an extension of the leg, or a straightening (extension) of the upper body. In all these movements, the upper leg element is swivelled relative to the upper body element in the second direction.

If the user of the orthopedic device wants to lift a heavy object, for example, he bends his knees and grabs the object. Here, both upper legs and therefore also the respective upper leg element are swivelled relative to the upper body and thus to the upper body element in the first direction. The angle between the upper leg and the upper body decreases. This causes the mechanical energy store to be charged with potential energy. To lift the object, the user of the orthopedic device must now extend his legs, wherein the upper leg is swivelled relative to the upper body in the opposite second direction. The potential energy stored in the mechanical energy store is released and supports the corresponding movement.

Preferably, the first swivel axes extend at least largely in frontal planes, but preferably in a common frontal plane. It is especially preferable if the first swivel axes extend through the hip joint of the user, so that the first ends of the rail elements are arranged laterally, i.e. externally. Conversely, the second ends of the rail elements are arranged dorsally, i.e. at the back, on the upper body element. The rail elements preferably extend in such a way that the first end is rotated by 90° relative to the second end. Here, the rail elements are preferably configured and arranged to be mirror-symmetrical to one another.

The second swivel axes preferably extend at least largely in the sagittal plane. Here, it is especially preferable for them to extend from dorsal to ventral, i.e. from back to front. As a result, an inclination of the body and the spinal column to the side is also possible without restricting the freedom of movement.

In a preferred configuration, the rail elements feature at least two partial rails, which are arranged on each other such that they can be swivelled about a third swivel axis. The three swivel axes preferably extend largely in sagittal planes. It is especially preferable if, when the orthopedic device is mounted, they extend largely parallel to the second swivel axes when the user of the orthopedic device stands upright. The swivel joints, which enable a movement of the partial rails relative to one another, are preferably arranged closer to the first end than the second end of the respective rail elements. It is especially preferable if these joints are positioned to the side of the body of the user, so that an imagined extension of the third swivel axis leads past the user's body.

When the orthopedic device is mounted, the second ends of the rail elements are preferably arranged in the region of the shoulder blades, but especially preferably in the region of the lower angles of the user's shoulder blades. When the spinal column bends right or left, this region exhibits the starkest deviation from a straight line, so that the joints, which connect the second ends to the upper body element in this region, are optimally positioned.

In a preferred configuration, a distance between joints, with which the second ends of the rail elements are arranged on the upper body element, is adjustable. The joints are preferably arranged on the upper body element such that they can be displaced. This is achieved, for instance, by arranging the respective joint on a slider that can be displaced along a guide, such as an elongated hole or link arranged in or on the upper body element.

Preferably, the second ends of the rail elements are arranged on the upper body element in such a way that they can be swivelled about two different swivel axes, one of which preferably extends in the dorsal-ventral direction and the other in the medial-lateral direction. The first of these two swivel axes allows the user of the orthopedic device to incline his upper body to the right and left, while the second of the two swivel axes is required to bend the user's upper body forwards or backwards.

In preferred embodiments, the two ends of the rail elements are arranged on the upper body element by means of ball joints. As a result, freedom of movement is further increased, as is the degree of acceptance of the orthopedic device by the user.

When the orthopedic device is mounted, the upper body element preferably extends completely around the user's upper body. It is preferably designed to be so dimensionally stable that its diameter in the medial-lateral direction does not or largely does not change when the upper body bends over. If the at least one mechanical energy store is to be charged with energy, the upper body element must be swivelled relative to the upper leg element. Where applicable, an activation device must also be activated, which may be achieved, for instance, via a movement of the upper body element relative to the pelvic element. If the energy store, which comprises a spring element for example, is charged, a force must be exerted, which can be caused by the upper body bending over. In the examples of embodiments specified, the upper body then exerts a tensile force on the upper body element.

The upper body element preferably comprises a chest section which, when the orthopedic device is mounted, rests on the user's chest at at least two spaced points on different sides of the user's sternum. The force is transmitted via these points from the upper body to the upper body element. Of course, this is also possible if the upper body element only comes into contact with the user's chest at a single point or at more than two points.

To charge the energy store with energy, a tensile force is exerted on the upper body element via the upper body and thus via the user of the orthopedic device. When the energy store is discharged, a tensile force is exerted on the upper body via the upper body element; said tensile force acts to support the user's lower back, for instance when straightening up. In this case, the tensile force is preferably transmitted via the rail elements to the upper body element and from here to the upper body. Since the rail elements are arranged dorsally, i.e. on the user's back, the tensile force is transmitted to the dorsal section of the upper body element and from there to the frontal section of the upper body element. This tensile force is transmitted to the upper body via the points at which this frontal section comes into contact with the upper body, i.e. preferably to the right and left of the user's sternum. Sufficient dimensional stability ensures that there is no constriction of the user's upper body when the tensile force is applied to the dorsal part of the upper body element. If the dimensional stability is too small, it is actually transferred to the upper body from frontal to dorsal through the parts of the upper body element that pass the sides of the upper body, like a sling to which a tensile force is applied. In this case, part of the force is transferred into a medially acting force, which can have painful effects.

Preferably, the part of the upper body element that surrounds the upper body is not completely dimensionally stable; rather, it exhibits a small degree of flexibility and preferably elasticity. This ensures that the orthopedic device and the upper body element is suitable for different people with different chest measurements, and can be designed to allow for the adjustment of this variable. It may be sufficient to connect individual rigid and inflexible elements to one another in a flexible and preferably elastic way, e.g. using half-shells or shell elements that surround parts of the upper body in a dimensionally stable and rigid manner. Alternatively, the upper body element can also be designed without any rigid elements.

In a preferred configuration, the orthopedic device features a first and a second upper leg element, and a first and a second mechanical energy store. Here, the first mechanical energy store can be charged and discharged by swivelling the first upper leg element relative to the upper body element. The second mechanical energy store can be charged and discharged by swivelling the second upper leg element relative to the upper body element. This configuration enables independent movement of the upper leg relative to the upper body element. The mechanical energy store only applies a force to the upper leg which has been swivelled relative to the upper body element.

Preferably, every upper leg element is arranged on the pelvic element by means of a joint arrangement such that it can be swivelled about a joint axis. The joint arrangement is preferably positioned in such a way that the joint axis extends through a hip joint of the user.

The upper leg element preferably features at least one mounting element for mounting it on the upper leg and at least one compressive force transmission element, via which the mounting element is connected to the joint arrangement. In a preferred embodiment, the compressive force transmission element is a rod or rail; it is particularly preferable if it is ergonomically formed.

The mounting element is preferably connected to each joint arrangement by at most one compressive force transmission element.

It is advantageous if each of the rail elements used is arranged on the upper body element such that it can be swivelled about at least two swivel axes, wherein at least two of the swivel axes are preferably perpendicular to each other.

It is particularly preferable if at least one of the rail elements is arranged on the upper body element via a ball joint. All rail elements are preferably each arranged on the upper body element via one ball joint.

Preferably at least one rail element, but especially preferably every rail element, is arranged on the respective joint arrangement, which is arranged on the pelvic element, such that it can swivelled about an axis of movement, wherein the axis of movement is preferably perpendicular to the joint axis of the respective joint arrangement.

The various movable configurations are designed so that the movements of the user's upper body, and in particular the spinal column, can be followed and, irrespective of the position of the upper body element relative to the pelvic element and/or relative to the at least one upper leg element, the force applied by the mechanical energy store in the charged state can act.

In an especially preferred configuration, the at least one rail element is designed to be adjustable in length. It is particularly preferable if all rail elements are adjustable in length. The orthopedic device can thus be used for people of different sizes. The length-adjustable rail element can preferably be fixed at different length settings, so that the length can be adjusted but then remains unchangeable.

The mechanical energy store preferably comprises at least a spring element, a pressure accumulator, a pneumatic and/or hydraulic system and/or a hydraulic energy store. Elastic elements in the form of elastic cords, such as rubber cords, are also conceivable. Of course, other elements, such as gas springs or compression springs, are also conceivable, for which a deflection is used to transform the compressive force coming from the compression spring into a tensile force.

The mechanical energy store can be arranged at various positions on the device. Preferably, a position is selected at which the installation space required for the energy store is available and the energy store does not cause any disruption, even while the user's leg is moving. For instance, it may be arranged on the upper leg.

For arranging the upper body element on the user's upper body, a shoulder element for mounting on the shoulder, which can be in the form of rucksack straps or braces, for example, is particularly suitable. It allows for an especially small design of the orthopedic device.

The upper leg element preferably comprises an upper leg shell that is preferably arranged on a spacer element. This spacer element, as part of the upper leg element, is preferably connected to the pelvic element. The lengths of the compressive force transmission element, which is designed as a rail or rod for example, and where applicable of the spacer element, which is also designed as a rod or rail, are preferably selected such that the entire angular range of the potential movement of the wearer's lower leg is covered. The upper leg shell is preferably flexibly arranged on the spacer element to render the device as comfortable as possible to wear.

In a preferred configuration, the passive actuator is configured to generate a force, irrespective of a position and/or orientation of the at least one leg support element relative to the pelvic element and/or the upper body element.

In a preferred configuration, the upper leg shell for mounting on the user's upper leg is preferably arranged on the upper leg element, but preferably on each upper leg element. Said shell is preferably designed to be padded to render it as comfortable as possible to wear. The upper leg shell is preferably arranged by means of a ball joint. This ensures the greatest possible freedom of movement in relation to the rest of the device, which is particularly advantageous when the user moves. By means of the ball joint, the upper leg shell can be arranged directly on a rail element or spacer element of the upper leg element. Alternatively, it is positioned on a holding bracket.

The upper leg shell can preferably be swivelled relative to the upper leg element about a rotational axis, preferably against a force of a spring element, wherein the rotational axis preferably extends in the medial-lateral direction. This is rendered particularly feasible by way of the positioning of the upper leg shell on the holding bracket, which is arranged on another component of the upper leg element such that it can be swivelled about the rotational axis.

The orthopedic device preferably comprises a joint with a first joint element, which has a first joint arm with a first positive-locking element, and a second joint element that can be swivelled relative to the first joint element, said second joint element comprising a second joint arm and a force application lever with a second positive-locking element and a mechanical energy store, which is arranged between the force application lever and the second joint arm, wherein the mechanical energy store can be charged and discharged by swivelling the first joint arm relative to the second joint arm when the first positive-locking element is engaged with the second positive-locking element. Preferably, the device has a safety device which ensures that, irrespective of the position of the first positive-locking element and the second positive-locking element relative to one another, the two positive-locking elements can be engaged with one another in such a way that a force exerted by the charged mechanical energy store is transmitted from the second positive-locking element to the first positive-locking element. This ensures that the uncontrolled release of energy when the positive-locking elements slip against each other is prevented.

The positive-locking elements preferably refer to the force transmission elements described above. The first joint element and the second joint element are preferably assigned respectively to the upper body element and the upper leg element or vice-versa.

The positive-locking elements feature recesses and/or projections that are designed in such a way that the two positive-locking elements can be positively engaged with one another. They are preferably gearwheels, particularly spur gearwheels.

In principle, different mechanisms with which the safety device solves the posed problem are conceivable. The safety device is preferably configured to rotate the positive-locking elements relative to one another when or after the two positive-locking elements are engaged with one another. If, at the point at which they should be engaged with one another, the positive-locking elements have positioned themselves in relation to one another in such a way that the projections and/or recesses of the two positive-locking elements can only be brought into engagement with each other in a small region rather than fully, the rotation of the two positive-locking elements relative to one another can change this relative position, thereby ensuring complete or at least greater engagement.

The first positive-locking element and the second positive-locking element preferably feature frontal projections and/or recesses. This is the case, for instance, with spur gearwheels. A spur gearwheel is understood to mean a gearwheel whose teeth protrude in the axial direction. The teeth of conventional gearwheels are arranged on the outer circumference of the gearwheel and protrude in the radial direction. A gearwheel has a rotational axis, about which it is rotatably mounted and in relation to which the terms axial and radial are to be understood. Conversely, the teeth of a spur gearwheel are situated on a front surface of the gearwheel and therefore protrude in the axial direction. If two such spur gearwheels are engaged with one another, all the teeth of one gearwheel preferably engage with the teeth of the other gearwheel, resulting in a considerably larger contact area than with conventional gearwheels, whose teeth are arranged on the external circumference. This allows a greater force to be transmitted.

If two such spur gearwheels whose teeth are not optimally positioned in relation to one another are engaged with one another, this can therefore be corrected by rotating the two gearwheels relative to each other. In this case, the required rotation is preferably small, specifically smaller than 5°, preferably smaller than 3°, especially preferably smaller than 2°. This also applies to positive-locking elements that are not gearwheels with teeth, but which feature other recesses and/or projections.

It is especially preferable if the safety device features a guide spindle that protrudes axially from one of the positive-locking elements and which has frontal recesses and/or projections, specifically spur gearing that is configured to engage with the respective other positive-locking element.

It is advantageous if the guide spindle can be displaced in the axial direction relative to the positive-locking element from which it protrudes axially, the guide spindle being designed in such a way that, upon axial displacement, the guide spindle is rotated about its longitudinal axis such that a torque is applied to the positive-locking element that engages with the frontal projections and/or recesses of the guide spindle. In such a configuration, the guide spindle protrudes axially from the front surface of one of the two positive-locking elements when the two positive-locking elements are not engaged with one another. If the two positive-locking elements are now to be brought into engagement with one another, one of the two positive-locking elements—preferably the one with no guide spindle protruding from it—moves towards the respective other positive-locking element. The frontal projections and/or recesses, in particular the spur gearing of the guide spindle, first come into contact with the frontal recesses and/or projections of the other positive-locking element. However, this does not stop the movement of the other positive-locking element towards the positive-locking element with the guide spindle: rather, the guide spindle is displaced in the axial direction and moved into the positive-locking element on which it is arranged.

Preferably the frontal projections and/or recesses, in particular the spur gearing of the guide spindle with the frontal recesses and/or projections, in particular with the spur gearing of its positive-locking element, form a continuous toothing when the guide spindle is displaced into its gear wheel to such an extent that a single continuous front surface is formed.

If the projections and/or recesses of the other positive-locking element, which has been displaced towards the guide spindle, do not engage optimally in its projections and/or recesses, a torque acts on this positive-locking element via the guide spindle, thereby rotating it into the optimal position for engaging in the recesses and/or projections of the other positive-locking element. This optimal position is reached when the guide spindle is completely recessed in its positive-locking element. This ensures that the projections and/or recesses of the two positive-locking elements engage with one another in the optimal position relative to one another, irrespective of the position of the two positive-locking elements relative to one another when they are to be brought into engagement.

Alternatively or additionally, the first positive-locking element and/or the second positive-locking element has two partial positive-locking elements, such as two partial gearwheels, which can be moved independently of each other in the axial direction. If the two positive-locking elements in this configuration are moved towards one another in order to engage them, one of the partial positive-locking elements of a positive-locking element engages in the projections and/or recesses of the other positive-locking element before the other partial positive-locking elements do the same. The partial positive-locking elements are preferably arranged at an offset to each other in the circumferential direction, so that the projections and/or recesses, particularly teeth of each of the partial positive-locking elements, are arranged equidistant from one another, but there is an angular offset between the projections and/or recesses, particularly between teeth of adjacent partial positive-locking elements. This ensures that the projections and/or recesses of different partial positive-locking elements engage with the projections and/or recesses of the other positive-locking element to varying degrees when the two positive-locking elements are brought into engagement with one another.

Therefore, if the projections and/or recesses of the first partial positive-locking element engage optimally in the projections and/or recesses of the other positive-locking element, it is sufficient for transmitting the forces that are to be applied. However, if this is not the case, since the projections and/or recesses of the first partial positive-locking element are only engaged with the other recesses and/or projections of the other positive-locking element in the vicinity of the tips, for instance, the projections and/or recesses of one of the other partial positive-locking elements engages more effectively in the other positive-locking element. If the contact between the tips of the projections and/or recesses of the first partial positive-locking element and the tips of the projections and/or recesses of the other positive-locking element is not enough to securely transmit the acting forces, the two positive-locking elements "slip". However, after a relative movement of just a few degrees, this is absorbed by the projections and/or recesses of one of the other partial positive-locking elements, which engage better in the projections and/or recesses of the other partial positive-locking element due to the angular offset between the projections and/or recesses of different partial positive-locking elements.

The at least two partial positive-locking elements therefore preferably feature the same projections and/or recesses, in particular the same toothing, but offset from each other in the circumferential direction. The offset is preferably smaller than 10°, preferably smaller than 7°, especially preferably smaller than 5°. In this context, the same toothing means that the teeth have the same depth, the same flank profile and the same angular offset to each other.

In a preferred configuration, the at least two partial positive-locking elements are spaced apart from one another in the axial direction when the first positive-locking element and the second positive-locking element are not engaged with one another. In this way, it is ensured which of the at least two partial positive-locking elements is the first partial positive-locking element to come into contact with other positive-locking elements.

In this case, a partial positive-locking element is shaped like a piece of pie. It preferably has two straight edges and one curved edge. It is preferably a segment of a circle. The toothing, which is preferably also shaped like a segment of a circle, is preferably situated on the front surface.

Preferably, the first joint element is allocated to the upper body element and the second joint element to the upper leg element. The device also features a pelvic element, wherein the two positive-locking elements can be brought in and out of engagement with one another by moving the upper body element relative to the pelvic element. This configuration of the invention is based on the knowledge that the lower back does not always need supporting when an angle between an upper body element, which is arranged, for instance, in the chest or back area of the upper body of the wearer, and the lower leg of the wearer is smaller than a predetermined angle, i.e. when the two body parts are swivelled against one another. Rather, support is only necessary when a swivelling occurs between the upper body, i.e. the chest, of the wearer, and the pelvis of the wearer. This configuration of the device thus ensures that a supporting force is always exerted when this swivelling between the upper body and the pelvis of the wearer occurs. Conversely, if the upper body swivels relative to the upper leg such that it does not cause a movement of the upper body relative to the pelvis, a force should not be exerted. In this case, the two gearwheels are not engaged with one another.

Preferably, at least two magnets are arranged on the pelvic element or the upper leg element and at least one magnet is arranged on the respective other element in such a way that they exert a force on one another, the direction of which changes when, during a movement of the upper body element relative to the pelvic element, the angle passes the predetermined limit angle. In this configuration, the displacement device thus features the magnets specified. On the element on the upper body element or the pelvic element on which two magnets are arranged, said magnets are preferably arranged in a different orientation. This means that for at least one of the magnets, the north pole is directed towards the respective other element of the orthopedic device, and for at least one other magnet, the south pole is directed towards the respective other element.

If the angle between the upper body element and the pelvic element is greater than the predetermined limit angle, the two positive-locking elements are not engaged with one another. The magnets preferably cause the application of a force that keeps the two positive-locking elements apart. This may be achieved by the magnets exerting a force on one another. For example, this may be a repelling force. This is achieved by positioning one magnet of the pelvic element and one magnet of the upper leg element close to each other, so that the same poles, i.e. the south pole or the north pole, are directed towards one another. If the pelvic element is now moved relative to the upper leg element, the magnets arranged on the respective elements are also moved. This results in a displacement of the moving magnets towards each other. At the point at which the angle of the upper body element relative to the pelvic element passes the predetermined limit angle, a second magnet of the pelvic element or the upper leg element preferably moves into the range of the at least one magnet of the respective other element. This results in an attractive force, as opposite poles of the two magnets are directed towards one another.

Preferably, at least some, but preferably all, projections and/or recesses of one of the positive-locking elements, but preferably of both positive-locking elements, feature undercut-toothing. This means that both flanks of a recess and/or projection are preferably tilted in the same direction. As a result, a torque can be applied to one of the positive-locking elements by the transmitted forces alone, which is converted into a force that has an axial component. This pulls the two positive-locking elements closer together, thus increasing the strength of the toothing, i.e. the engagement of the two positive-locking elements with each other.

The positive-locking elements can preferably be brought into engagement with each other by moving one of the positive-locking elements towards the other positive-locking element, which is mounted relative to the component on which it is arranged such that it can be rotated in one direction. This is preferably a floating bearing, which allows a slight rotation of, for example, less than 15°, preferably less than 10°, particularly preferably less than 5°, thus ensuring that the optimum position and orientation of the two positive-locking elements relative to each other can be achieved.

BRIEF DESCRIPTION OF THE DRAWINGS

In the following, examples of embodiments of the present invention will be explained in more detail by way of the attached figures: They show FIGS. 1 and 3—a schematic side view and rear view of a part of a device according to a first example of an embodiment of the present invention, FIGS. 2 and 4—enlarged representations of parts of FIGS. 1 and 3, FIGS. 5 to 7—a device according to an example of an embodiment of the present invention in the mounted state, FIG. 8—the schematic depiction of different force patterns as a function of the angle between upper leg element and upper body element.

Figure 1:
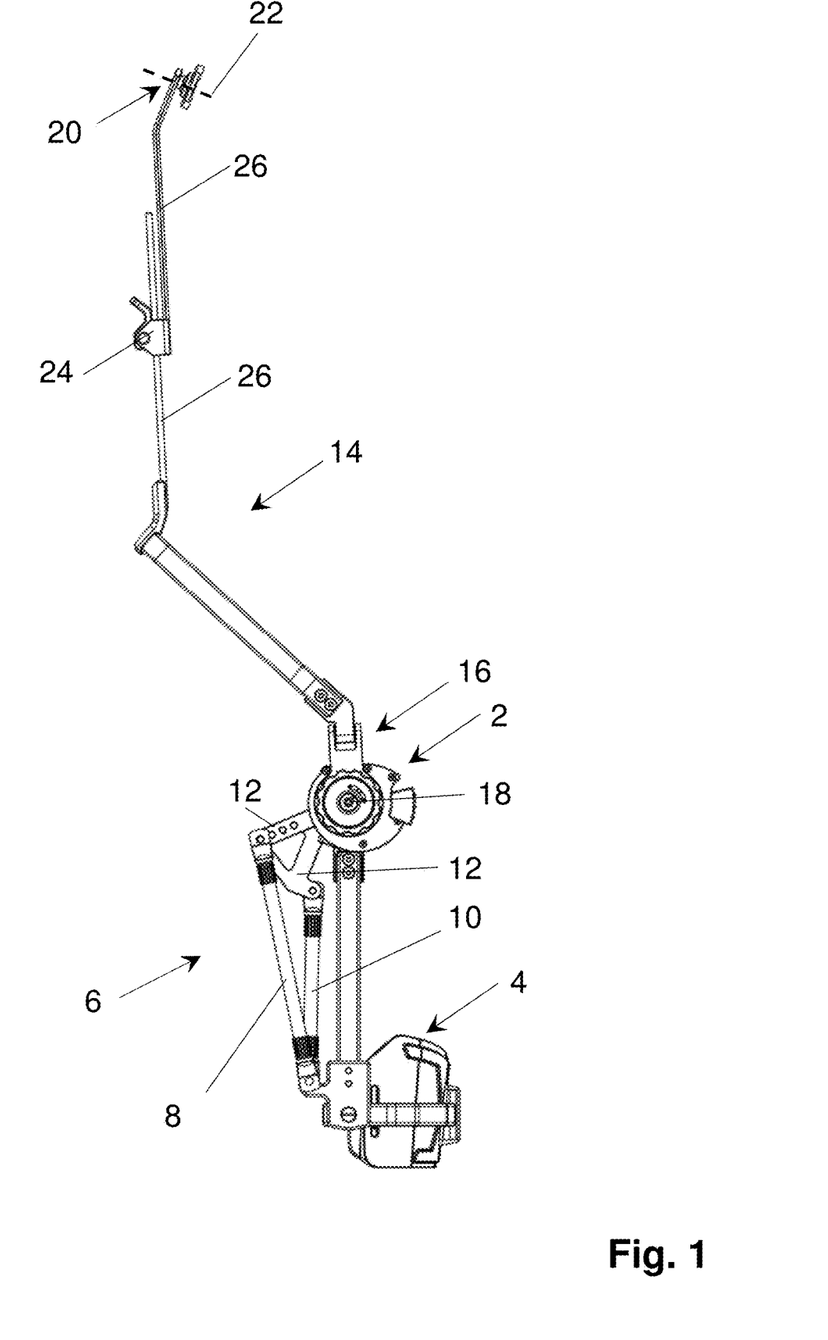

FIG. 1 depicts a side view of a part of a device according to a first example of an embodiment of the present invention. The device features a pelvic element 2, an upper leg element 4 and a mechanical energy store 6. The mechanical energy store 6 comprises a first passive actuator 8 and a second passive actuator 10, which can be connected to the pelvic element 2 via two force application levers 12 such that they are torque-proof. A rail element 14 is positioned on the pelvic element 2, wherein the first end 16 of said rail element is arranged on the pelvic element 2 such that it can be swivelled about a first swivel axis 18. In the example of an embodiment shown, the first swivel axis 18 extends perpendicular to the drawing plane. A second end 20 is arranged on an upper body element, not depicted, such that it can be swivelled about a second swivel axis 22. The length of the rail element 14 can be adjusted via an adjustment device 24, which is designed as a clamping device in the example of an embodiment shown. To this end, in the example of an embodiment shown, two sections 26 are displaced against each other as soon as the adjustment device 24 has been released. The adjustment device is subsequently re-locked and the rail element 14 used in the amended length.

Figure 2:
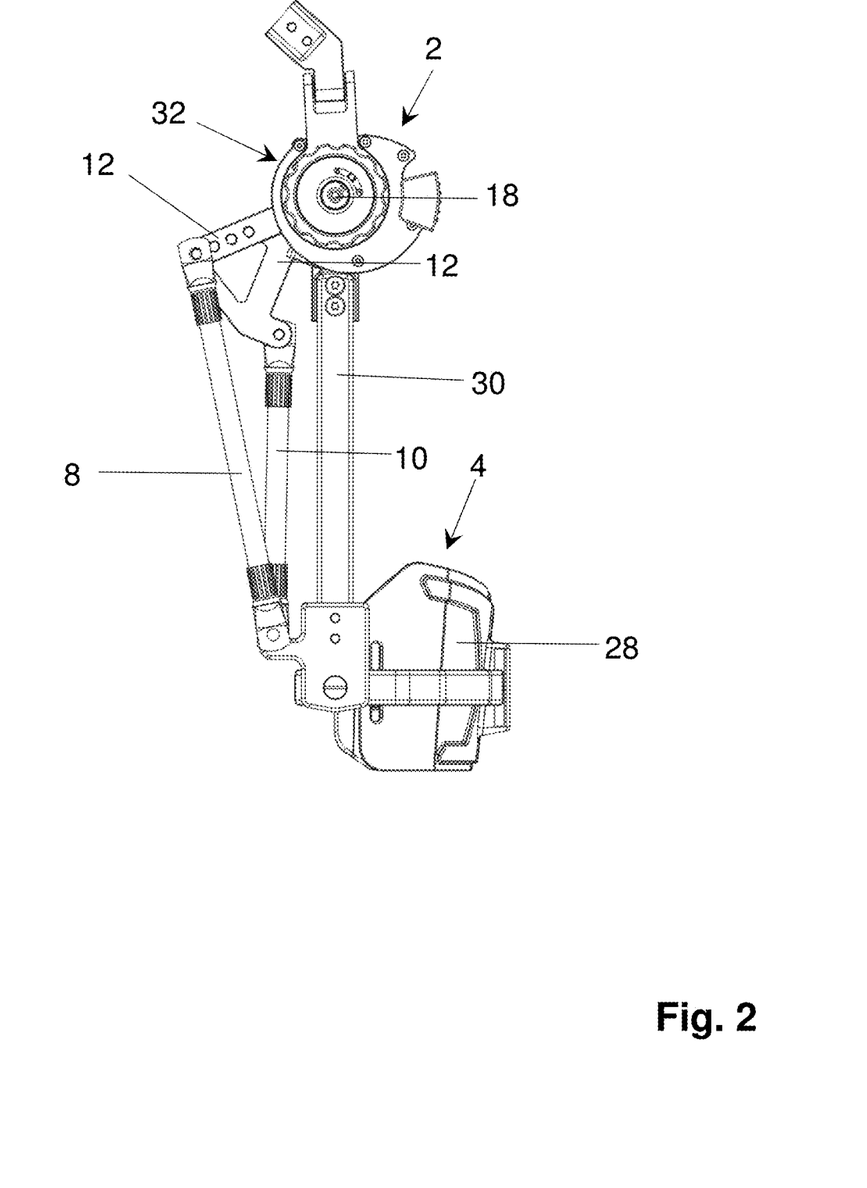

FIG. 2 shows an enlarged section from FIG. 1. The upper leg element 4 comprises a leg shell 28 that is arranged on a spacer element 30. A joint arrangement 32 allows the upper leg element 4 to be swivelled relative to the pelvic element 2. The joint arrangement 32 can preferably be brought into a passive position and an active position. In the passive position, the force application levers 12 can be moved relative to the rest of the pelvic element 2. If, in this state, the upper leg element 4 is moved relative to the pelvic element 2, a force is applied to the force application levers 12 via the first passive actuator 8 and the second passive actuator 10 which ensures that the force application levers 12 are swivelled with the upper leg element 4. When the joint arrangement 32 is in the active state, the force application levers 12 are connected to the pelvic element 2 such that they are torque-proof. It is therefore not possible to swivel the force application levers 12 with the upper leg element 4 when it is moved relative to the pelvic element 2. The passive actuators 8, 10 are thus tensioned. Due to the different force application levers 12 and the different length of the two passive actuators 8, 10, the actuators contain different forces at different angular positions.

Figure 3:
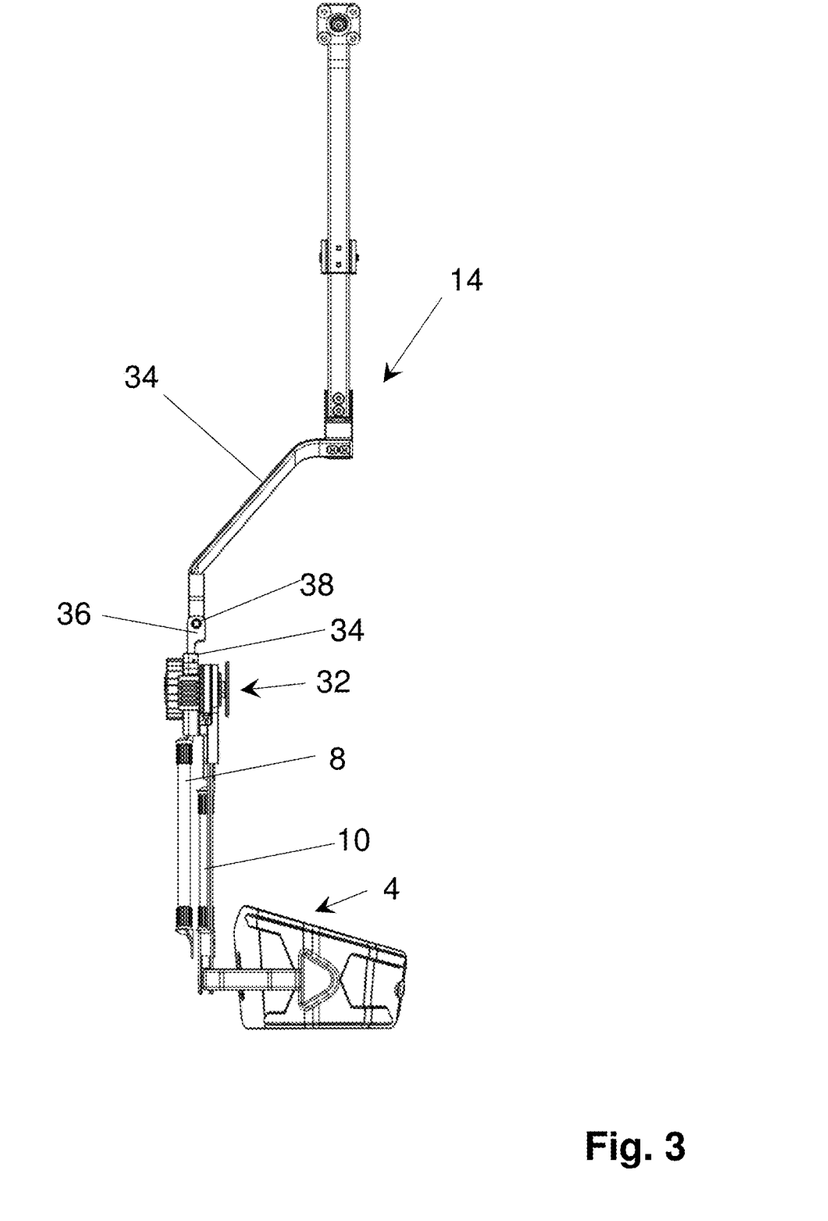

FIG. 3 depicts a rear view of the device from FIG. 1. The upper leg element 4 with the first passive actuator 8 and the second passive actuator 10, the joint arrangement 32 and the rail element 14 are all clearly recognizable. The rail element 14 features two partial rails 34 which are connected to a third swivel axis 38 via a joint 36.

Figure 4:
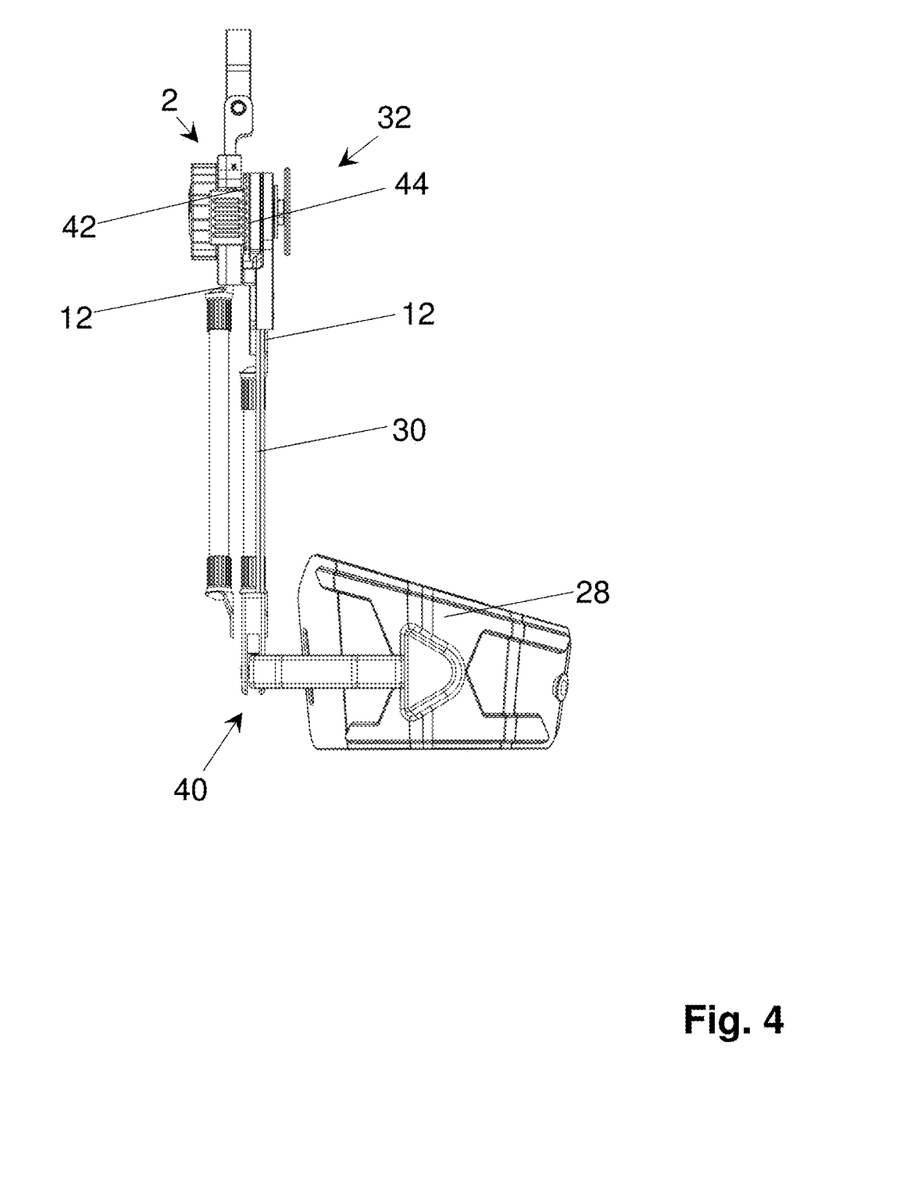

FIG. 4 shows an enlarged section from FIG. 3. The leg shell 28 is positioned on the spacer element 30 via a positioning device 40 such that it can be swivelled in at least one direction, so that the optimal position of the leg shell 28 relative to the user's upper leg can be selected. In the example of the embodiment shown, the joint arrangement 32 is in the passive position. A first force transmission element 42 and a second force transmission element 44 can be recognized, which are not engaged with one another in the position shown. The force application levers 12 are thus not connected to the pelvic element 2 in a torque-proof manner.

Figure 5:
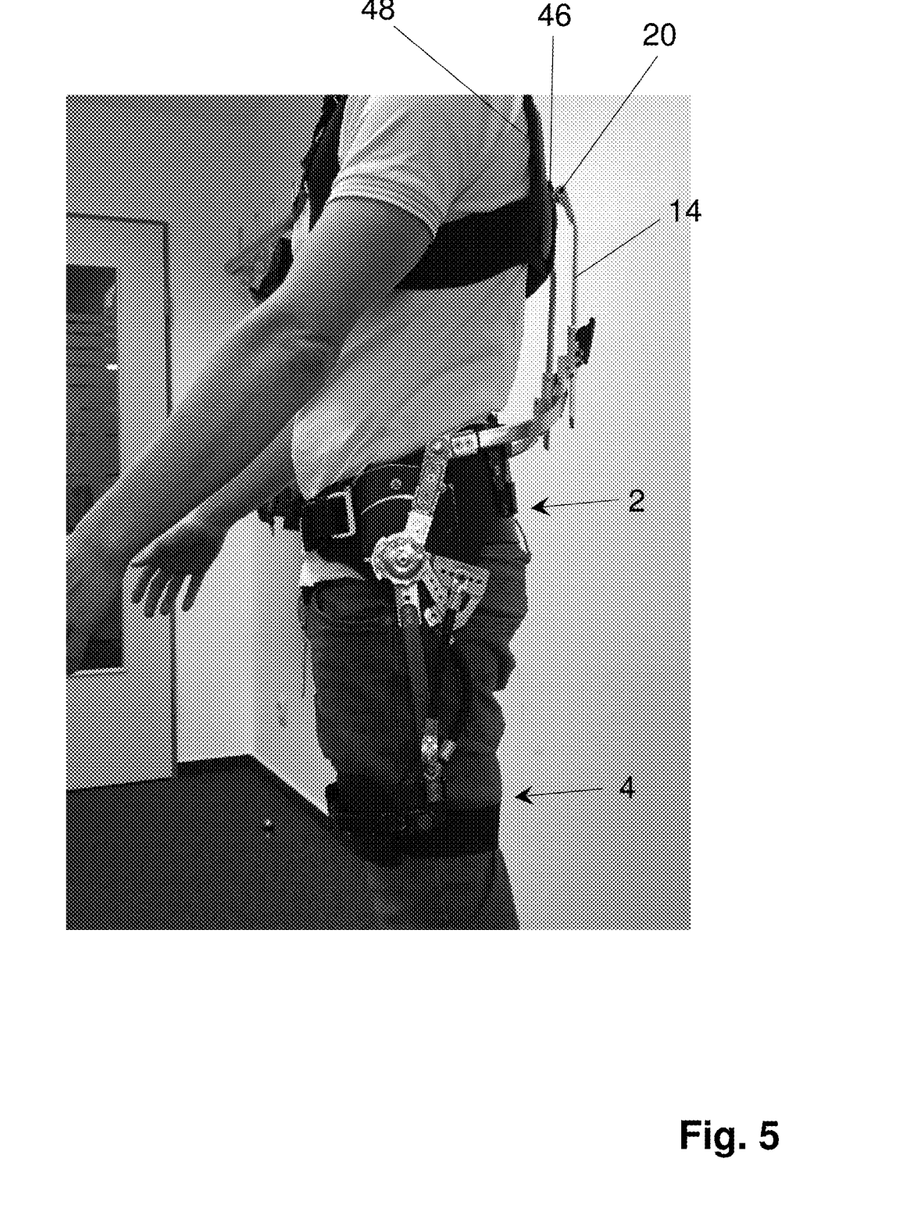
Figure 6:
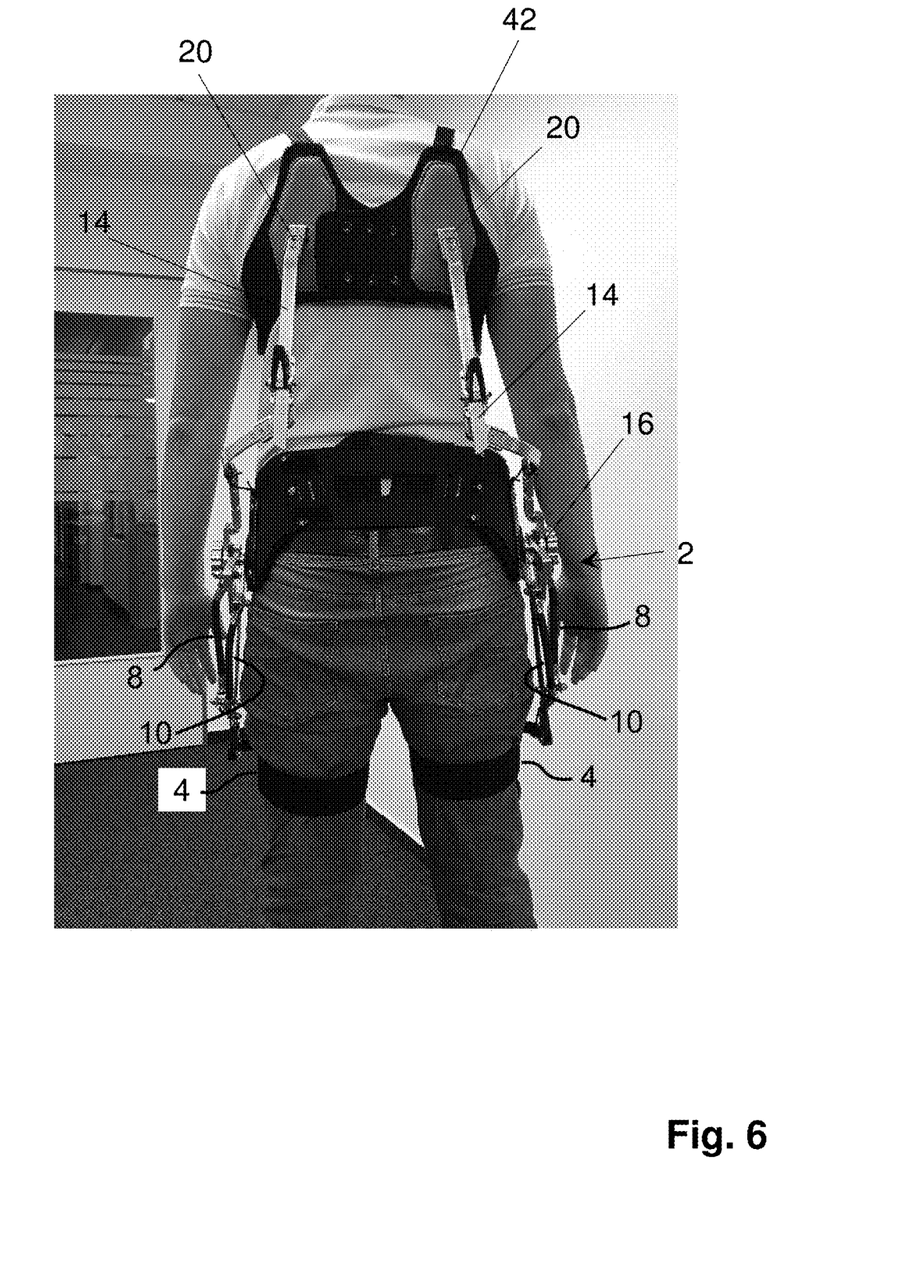
Figure 7:
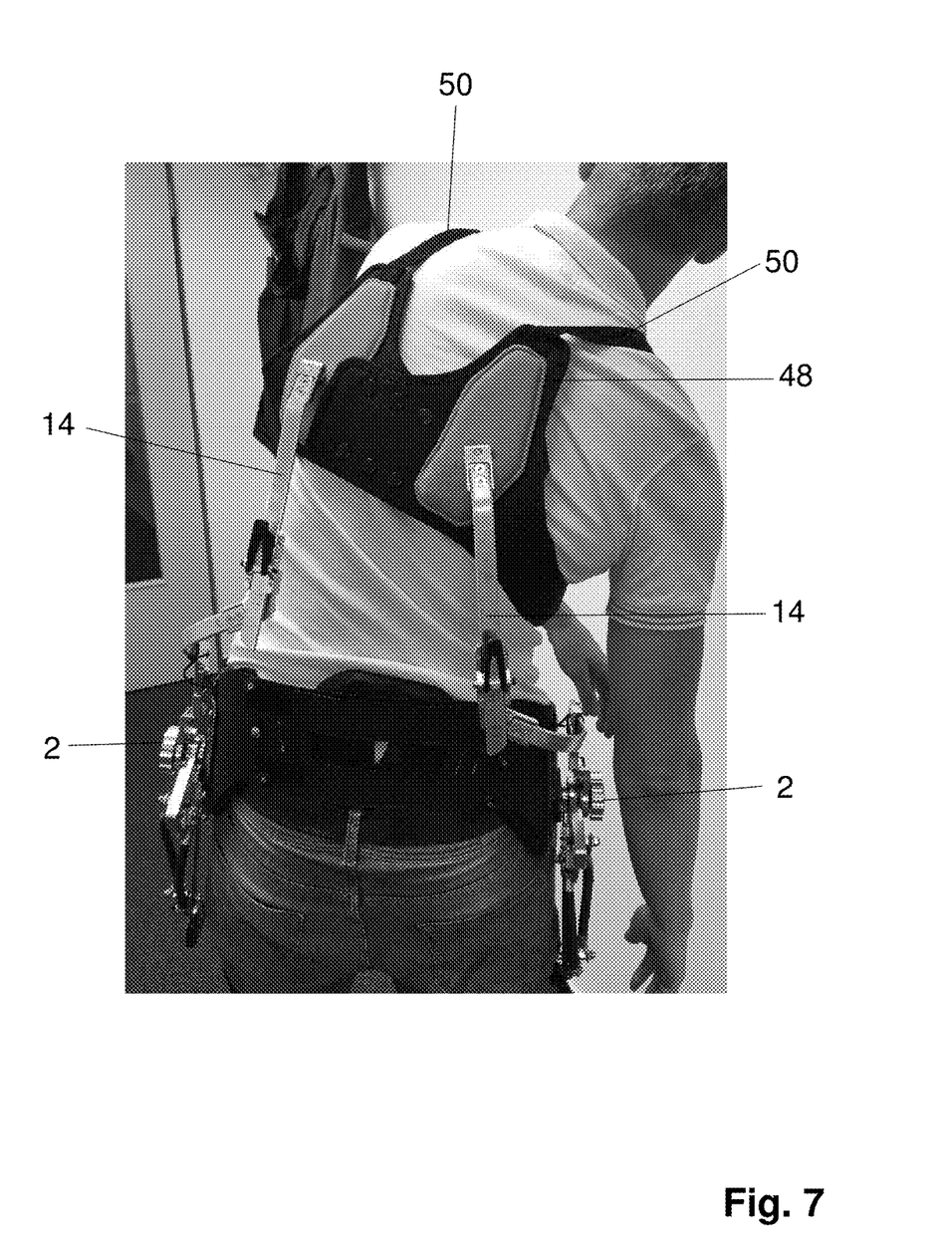

FIGS. 5 to 7 show a device in the mounted state. FIG. 5 depicts a side view of the user. The upper leg element 4, the pelvic element 2 and particularly the rail elements 14 can be recognized. At the second end 20, the rail elements are arranged on the upper body element 48 via a ball joint 46.

FIG. 6 shows a rear view of the device in the mounted state. The two rail elements 14 extend from their second end 20, starting from the upper body element 48, to the pelvic element 2, where the first end 16 is arranged. It shows that the second ends 20 are arranged dorsally, i.e. on the back, on the upper body element 48, while the first ends 16 are arranged laterally, i.e. at the side, on the pelvic element 2.

FIG. 7 depicts the situation with a spinal column that is inclined to the right. The upper body element 48 moves slightly relative to the upper body, which is enabled by the two straps 50, which can also be described as shoulder straps. At the same time, the rail elements 14 swivel relative to the pelvic element 2, thereby enabling considerable freedom of movement. Both the upper body element 48 and the pelvic element 2, which includes a pelvic harness 52, are adjustable in length and can therefore be used for different people.

Figure 8:
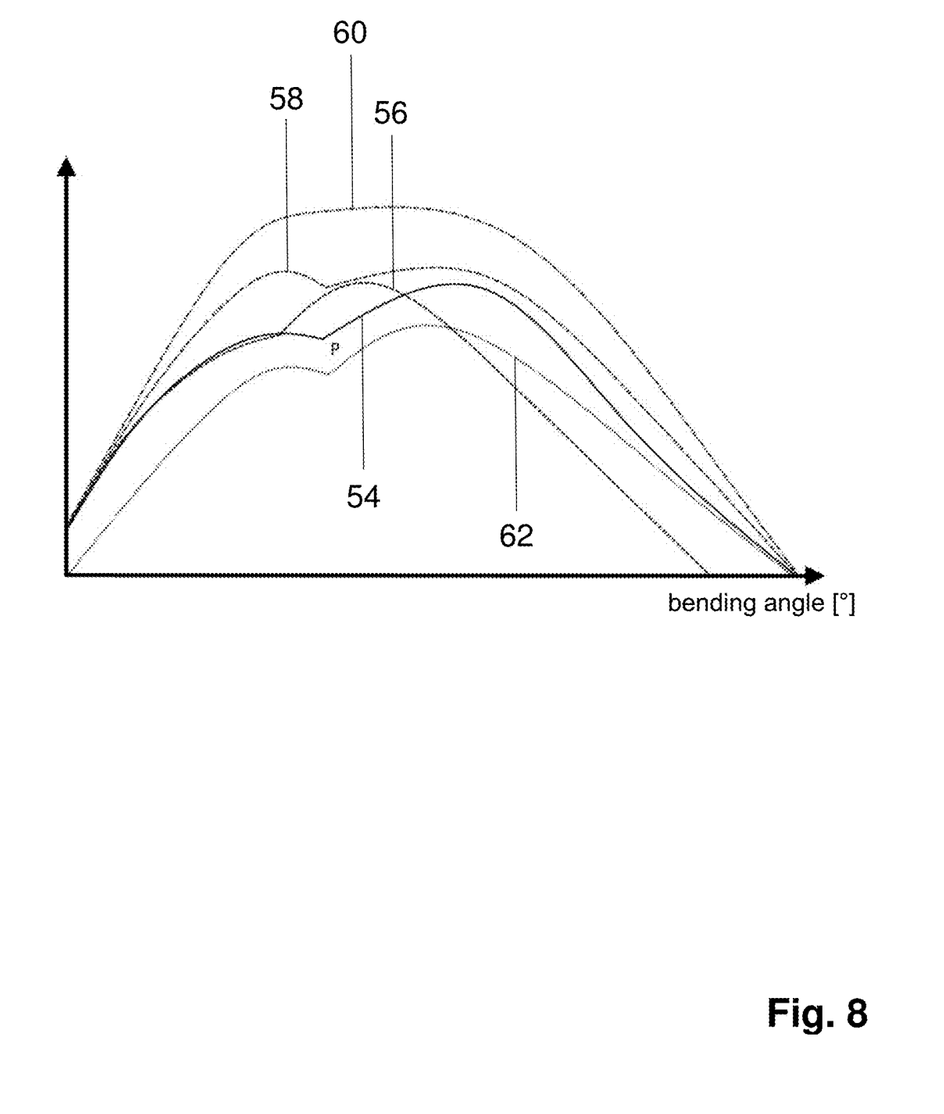

FIG. 8 depicts various force patterns, which can be interpreted as torque patterns, of the force exerted by the first actuator 8 and the second actuator 10 as a function of the angle between the upper leg element 4 and the upper body element 48. The solid line 54 does not start at the origin of the coordinate system. Consequently, the force applied is not equal to 0, even outside the first predetermined angular range, provided the angle is greater than the predetermined angular range. For example, the angle is greater when the person is standing upright. In the example of an embodiment shown, the first passive actuator 8 is therefore preloaded and exerts a force. This forces increases as the bending angle increases, i.e. as the angle between the upper leg element 4 and the upper body element 48 decreases, until it reaches a first maximum. If the bending continues, i.e. the angle decreases further, the force reduces again until the force begins to increase again at point P. The predetermined second angular range, in which the second passive actuator 10 exerts its force, begins in this range. This initially increases until the solid line 54 reaches its global maximum. At this bending angle, both the first passive actuator 8 and the second passive actuator 10 generate a force. These forces decrease upon further bending until no more force is exerted at the end.

The dashed curve 56 depicts a similar situation. In contrast to the solid line 54, the angle between the two force application levers 12 has been reduced. This is achieved, for example, by displacing the force application lever 12 in FIGS. 1 and 2, with which the second passive actuator 10 engages, anti-clockwise relative to the second force application lever 12, with which the first passive actuator 8 engages. It is clear that the point P has been displaced to the left. Consequently, the second passive actuator 10 already develops its force at smaller bending angles, i.e. greater angles between the upper leg element 4 and the upper body element 48.

The dash-dot line 58 shows another situation. In comparison to the solid line 54, the position of the two force application levers 12 relative to one another has not been changed. Rather, both force application levers 12 have been extended, causing an increase in the force exerted by the first passive actuator 8 and the second passive actuator 10 because the lever arm extends.

The dash-dot-dot line 60 shows the situation in which both the first passive actuator 8 and the second passive actuator 10 exert their force across the entire range.

The dotted line 62 corresponds to the parallel displaced solid line 54. The first passive actuator 8 is thus used without preloading.

REFERENCE LIST 2 pelvic element
4 upper leg element
6 mechanical energy store
8 first passive actuator
10 second passive actuator
12 force application lever
14 rail element
16 first end
18 first swivel axis
20 second end
22 second swivel axis
24 adjustment device
26 section
28 leg shell
30 spacer element
32 joint arrangement
34 partial rail
36 joint
38 third swivel axis
40 positioning device
42 first force transmission element
44 second force transmission element
46 ball joint
48 upper body element
50 strap
52 pelvic harness
54 solid line
56 dashed curve
58 dash-dot line
60 dash-dot-dot line
62 dotted line

The invention claimed is:

1. An orthopedic device for supporting a back of a user, wherein the orthopedic device comprises
an upper body element;
an upper leg element arrangeable on a single upper leg of the user;
a joint between the upper body element and the upper leg element, wherein the joint provides a pivot axis about which the upper body element and the upper leg element are pivotable relative to each other;
a first passive actuator which is configured to apply a first force to the upper leg element when an angle between the upper leg element and the upper body element is within a first predetermined angular range;

a second passive actuator which is configured to apply a second force to the upper leg element when the angle is within a predetermined second angular range that is different to the first predetermined angular range, wherein the first passive actuator and the second passive actuator apply their respective forces in a same direction to the upper leg element.

2. The orthopedic device according to claim 1, wherein at least one of the first passive actuator and the second passive actuator comprises at least one mechanical energy store.

3. The orthopedic device according to claim 2, wherein the at least one mechanical energy store comprises elastic elements, wherein the elastic elements of the first passive actuator and the second passive actuator exhibit different elasticities.

4. The orthopedic device according to claim 3, wherein the elastic elements of the first passive actuator and the second passive actuator exhibit at least one of different spring constants and different degrees of damping.

5. The orthopedic device according to claim 2, wherein the at least one mechanical energy store includes at least a first mechanical energy store and at least a second mechanical energy store, wherein the upper body element comprises a first force transmission element and the upper leg element comprises a second force transmission element, wherein the first mechanical energy store and the second mechanical energy store are chargeable and dischargeable by swivelling the upper leg element relative to the upper body element when the first force transmission element is engaged with the second force transmission element.

6. The orthopedic device according to the claim 5, further comprising a pelvic element and wherein the upper body element is arranged such that it is movable relative to the pelvic element, wherein the first force transmission element is engageable and disengageable with the second force transmission element by moving the upper body element relative to the pelvic element.

7. The orthopedic device according to claim 2, wherein the at least one mechanical energy store is at least one elastic element.

8. The orthopedic device according to claim 2, wherein the at least one mechanical energy store comprises one or more of at least one tension spring and at least one damper.

9. The orthopedic device according to claim 1, wherein the first passive actuator and the second passive actuator are each arranged at at least one force application point on at least one force application lever.

10. The orthopedic device according to the claim 9, wherein the at least one force application lever comprises at least two force application levers, wherein at least one of an orientation and a position of the two force application levers in relation to one another is adjustable.

11. The orthopedic device according to claim 10, wherein at least one of the orientation and position of the at least two force application levers in relation to force application points for the at least two force application levers are adjustable.

12. The orthopedic device according to claim 9 wherein the at least one force application point include at least two force application points, and wherein at least one of the two force application points is adjustable.

13. The orthopedic device according to claim 1, wherein at least one of a first pattern of force applied by the first passive actuator and a second pattern of force applied by the second passive actuator is dependent on the angle between the upper leg element and the upper body element.

14. The orthopedic device according to claim 13, wherein the angle varies between different angles, and wherein the first force exerted by the first passive actuator and the second force exerted by the second passive actuator exhibit a maximum at the different angles.

15. The orthopedic device according to claim 13, wherein at least one of the first pattern of force applied by the first passive actuator and the second pattern of force applied by the second passive actuator is curved.

16. The orthopedic device according to claim 13, wherein the pattern of force applied by at least one of the first passive actuator and the second passive actuator is sinusoidal.

17. The orthopedic device according to claim 1, wherein the first angular range and the second angular range overlap.

18. The orthopedic device according to claim 1, whereinone or more of the first passive actuator and the second passive actuator are arranged at at least one point of application on at least one of the upper leg element and the upper body element that is adjustable.

19. The orthopedic device according to claim 1, wherein the first passive actuator and the second passive actuator are arranged at different points of application on at least one of the upper leg element and the upper body element.

20. The orthopedic device according to claim 1, wherein a preload of at least one of the first passive actuator and a preload of the second passive actuator is adjustable.

21. The orthopedic device according to claim 1, wherein for angles smaller than a respective predetermined angular range, the force exerted by a respective passive actuator is zero.

22. The orthopedic device according to claim 1, wherein the first passive actuator and the second passive actuator have different lengths.

23. An orthopedic device for supporting a back of a user, wherein the orthopedic device comprises
an upper body element;
an upper leg element arrangeable on a single upper leg of the user;
a joint between the upper body element and the upper leg element, wherein the joint provides a pivot axis about which the upper body element and the upper leg element are pivotable relative to each other;
a first passive actuator which is configured to apply a first force to the upper leg element and the upper body element when an angle between the upper leg element and the upper body element is within a first predetermined angular range;
a second passive actuator which is configured to apply a second force to the upper leg element and the upper body element when the angle is within a second predetermined angular range that is different to the first predetermined angular range,
wherein the first passive actuator and the second passive actuator apply their respective forces in a same direction to the upper leg element and the upper body element.

24. The orthopedic device of claim 23 further comprising a first force application lever connected to the first passive actuator and a second force application lever connected to the second passive actuator.

25. An orthopedic device for supporting a back of a user, wherein the orthopedic device comprises
an upper body element;
a first upper leg element arrangeable on a left upper leg of the user;

a second upper leg element arrangeable on a right upper leg of the user;

a first joint between the upper body element and the first upper leg element and a second joint between the upper body element and the second upper leg element, wherein each joint provides a pivot axis about which the upper body element and each respective upper leg element are pivotable relative to each other;

a first passive actuator which is configured to apply a first force to the first upper leg element arrangeable on the left upper leg when a first angle between the first upper leg element and the upper body element is within a first predetermined angular range;

a second passive actuator which is configured to apply a second force to the first upper leg element arrangeable on the left upper leg when the first angle is within a second predetermined angular range that is different to the first predetermined angular range;

a third passive actuator which is configured to apply a third force to the second upper leg element arrangeable on the right upper leg when a second angle between the upper leg element and the upper body element is within a third predetermined angular range; and a fourth passive actuator which is configured to apply a fourth force to the second upper leg element arrangeable on the right upper leg when the second angle is within a fourth predetermined angular range that is different to the third predetermined angular range;

wherein the first, second, third and fourth passive actuators apply their respective forces in a same direction to a respective first or second upper leg element and the upper body element.

\* \* \* \* \*